US006760614B2

(12) United States Patent
Yonce

(10) Patent No.: US 6,760,614 B2
(45) Date of Patent: Jul. 6, 2004

(54) METHOD AND APPARATUS FOR P-WAVE ENHANCEMENT IN ECG RECORDINGS

(75) Inventor: David J. Yonce, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 488 days.

(21) Appl. No.: 09/957,043

(22) Filed: Sep. 20, 2001

(65) Prior Publication Data

US 2003/0055349 A1 Mar. 20, 2003

(51) Int. Cl.[7] .................................................. A61B 5/04
(52) U.S. Cl. ...................................................... 600/509
(58) Field of Search .............................. 600/509; 607/5, 607/9

(56) References Cited

U.S. PATENT DOCUMENTS 4,887,609 A   12/1989  Cole, Jr.
5,999,845 A  * 12/1999  dePinto .................... 600/509

* cited by examiner

Primary Examiner—Mark Bockelman
(74) Attorney, Agent, or Firm—Thomas J. Nikolai; Nikolai & Mersereau, P.A.

(57) ABSTRACT

To enhance the ability to visualize P-waves in surface ECG data, an algorithm is presented in which the ECG data is selectively passed through first and second signal processing channels where one of the channels includes signal processing elements for enhancing P-waves and the other channel provides a delayed version of the original data. Upon detection of an atrial pace event, the filtered or filtered and amplified data is inserted into the data stream in place of the raw input signal for a predetermined time interval sufficiently long to ensure the occurrence of an atrial depolarization signal.

22 Claims, 4 Drawing Sheets

METHOD AND APPARATUS FOR P-WAVE ENHANCEMENT IN ECG RECORDINGS

BACKGROUND OF THE INVENTION

I. Field of the Invention

This invention relates generally to ECG apparatus for recording and displaying ECG signals developed on a plurality of body contacting surface electrodes, and more particularly to an apparatus and method for enhancing the detection and recording of atrial depolarization events (P-waves) by selectively inserting appropriately signal processed ECG data into the ECG input data stream during a time interval in which P-wave activity is expected to occur.

II. Discussion of the Prior Art

Clinicians typically use a surface ECG to verify cardiac tissue cardiac tissue capture from an implanted pacemaker pulse. Because of the inherent low amplitude of atrial activity, P-waves are often difficult to observe on a surface ECG, especially in patients having diseased or damaged hearts. This has traditionally created a challenge for clinicians when assessing atrial capture by a pacemaker. Thus, a need exists for an ECG apparatus and a method of operating same in such a way that the detection of P-waves is enhanced. The present invention meets that need by providing real-time algorithms for enhancing the visibility of P-waves so that atrial capture by pacing pulses from an implanted cardiac rhythm management device (CRMD) can be assessed.

SUMMARY OF THE INVENTION

Conventional ECG systems filter data picked up by skin-contacting electrodes positioned at predetermined locations on a patient's body to a bandwidth of around 100 to 150 Hz. While the ventricular depolarization (R-wave) often contains frequencies up to 100 Hz, P-waves contain a lower spectral energy. By filtering the data stream to a bandwidth of 30 Hz or less, the signal-to-noise ratio can be increased when observing P-waves. Taking this into account, the algorithm of the present invention applies the ECG input signal train from a pair of skin-contacting electrodes to first and second signal processing channels where the first channel includes a low pass filter having a cut-off frequency capable of attenuating spectral energies characteristic of ventricular depolarization while passing spectral energies characteristic of atrial depolarization. The second channel comprises a signal delay configured to match the signal delay inherent in the low pass filter. The ECG input signal train is made to normally flow through the second channel, but upon detection of an atrial stimulating pulse produced by the implanted CRMD, the ECG input signal train is made to flow through the first channel for a predetermined time. By providing separate signal processing channels where the first channel includes a low pass filter having a cut-off frequency of about 30 Hz and the second channel includes an all pass filter that subjects the input ECG signal train to a delay corresponding to that of the low-pass filter, the 30 Hz data can be inserted in place of the 100 Hz data stream for a predetermined time interval, e.g., 150 to 200 milliseconds, following a detection of an atrial passing pulse. The 150 to 200 millisecond interval is sufficiently long that a P-wave should have been evoked if the amplitude of the atrial passing pulse results in capture.

The present invention also teaches a way in which the optimally filtered signal for observing P-waves can be seamlessly inserted into the 100 Hz data stream using a digital signal processing algorithm involving a weighted averaging technique.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
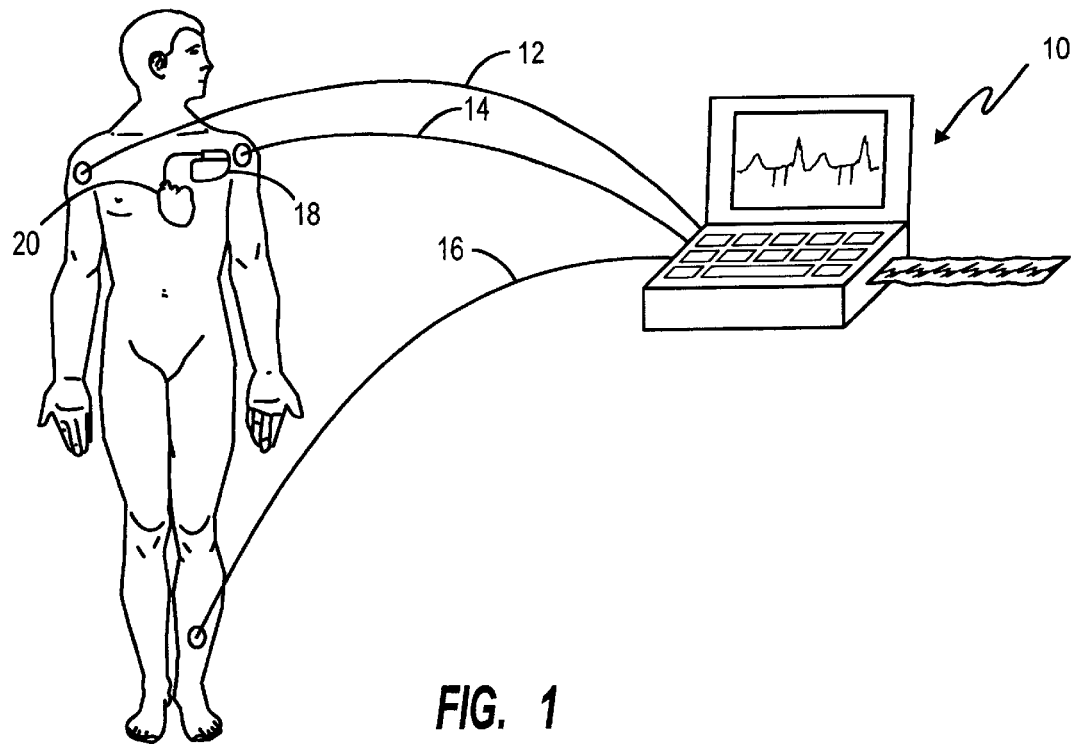
FIG. 1 illustrates an ECG apparatus connected by surface electrodes to a subject in whom a cardiac rhythm management device has been implanted.

Referring to FIG. 1, there is shown an ECG apparatus 10 which is connected by leads 12, 14 and 16 to a right arm electrode, a left arm electrode and a left leg electrode, respectively. The patient is shown as having an implanted dual chamber pacemaker 18 implanted for applying stimulating pulses to the heart 20 and for picking up signals originating in the heart muscle.

As had been pointed out earlier, standard ECG systems filter surface data to a bandwidth of about 100–150 Hz but that atrial depolarizations (P-waves) have spectral energies with a substantially lower bandwidth of about 30 Hz or less. Thus, it is often times difficult to discern the occurrence of P-waves on the ECG traces produced by the machine 10. In accordance with the present invention, there is provided algorithms for enhancing the visibility of P-waves in the ECG signal train. The algorithms employed are best understood by referring to the analog circuit arrangement illustrated in FIG. 2. It is to be understood, however, that the ECG apparatus 10 would typically be microprocessor-based such that the analog signals picked up on the body contacting electrodes are applied to the microprocessor, via an A/D converter (not shown) which samples the waveform at a relatively high rate and converts the amplitude of the sampled signals to digital quantities.

Figure 2:
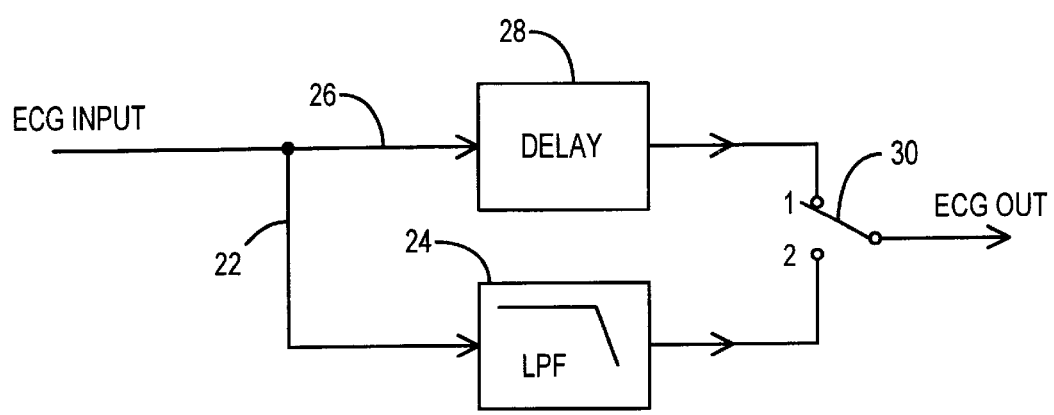
FIG. 2 is a schematic showing of a first algorithm used to enhance P-wave signals in the ECG input data stream.

As seen in FIG. 2, the input signal train is effectively applied to a first signal processing channel 22 that includes a low pass digital filter 24 and a second signal processing channel 26 including a delay 28. The incoming data stream normally passes along the channel 26 through delay element 28, but upon the implanted CRMD generating an atrial pace pulse, the ECG output is derived from the first channel 22 when the virtual switch 30 transfers from terminal 1 to terminal 2. Since the next event following the occurrence of an atrial pacing pulse is a P-wave, the low pass filter 24 is configured to optimize the filtering for P-waves. The switch 30 remains in the terminal 2 position for a predetermined time interval, typically in the range of from about 150 milliseconds to about 200 milliseconds. It has also been found expedient to set the time interval following the occurrence of an atrial pace to the programmed value of the AV delay established for the CRMD 18, assuming it to be a DDD device. Still another alternative is to end the predetermined time interval for the switch 30 to be at terminal 2 when a ventricular pace or a spontaneous ventricular depolarization (R-wave) occurs, whichever happens to be first.

The delay value for element 28 is made equal to the delay inherent in the low-pass filter 24. Thus, the delay block 28 maintains the higher frequency components of the incoming ECG data stream to thus insure the alignment of the two data streams in time exiting the processing blocks 24 and 28. For intrinsic ECG activity, the virtual switch 30 is in position 1, allowing the ECG data to pass unfiltered to the output. Following an atrial pace, the switch 30 changes to position 2, sending filtered data to the output for optimal viewing of P-waves.

Figure 3:
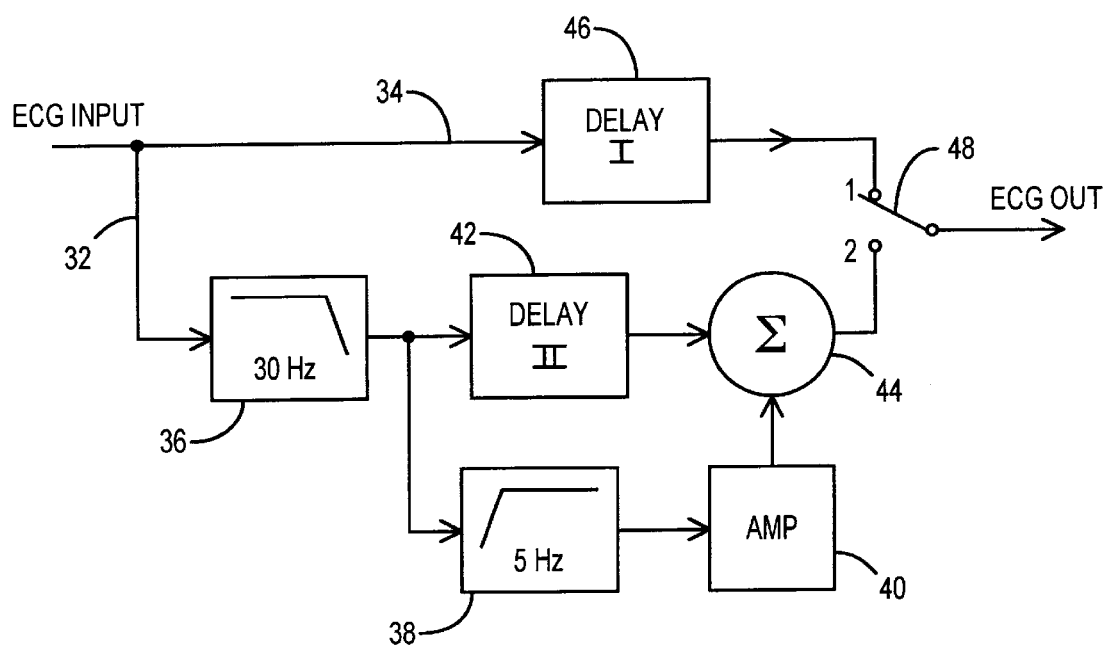
FIG. 3 is a schematic illustration helpful in understanding a second algorithm for enhancing the P-wave presentation on an ECG machine.

Referring next to FIG. 3, there is shown a second algorithm which provides optimally filtered and amplified P-waves in the ECG output data stream. Again, FIG. 3 represents the algorithm by means of analog components, but it is understood that, generally speaking, the processing involved occurs in the digital domain and that FIG. 3 is presented merely to assist the reader in an overall understanding of the operation of the algorithm involved. Those skilled in the art of digital signal processing can readily prepare software for execution by a microprocessor used in the ECG recorder that would execute the depicted functionality.

The algorithm depicted in FIG. 3 is a modification of the algorithm depicted in FIG. 2 that allows for amplification of the atrial signals to render them more discernible in an ECG trace. As in the earlier embodiment, the raw ECG input developed between a pair of selected ECG surface electrodes is applied to first and second signal processing channels 32 and 34, respectively. The first channel includes a low-pass filter 36 connected in series with a high pass filter 38 and an amplifier 40. The output of the low pass filter 36 is subjected to a predetermined delay at block 42 before being summed at 44 with the output of amplifier block 40. The second channel 34 includes an all-pass filter 46 that merely serves to introduce a predetermined delay to the input ECG signal.

The low pass filter will again typically have a cut-off frequency of about 30 Hz, a value which will enhance the spectral energy of P-waves while attenuating higher frequency components of the ECG input signal. The high pass filter 38 is provided to remove low frequency components from the ECG waveform. This high pass filter removes any baseline wander or DC bias from the original signal to prevent DC values from being amplified. A cut-off frequency for the high pass filter may be about 5 Hz. Because the minimal distortion of the baseline is critical for the summing application involved, linear phase filters should be utilized for the high pass filter 38. The delay block 42 serves to align the data from the high pass filter 38 and low pass filter 36, for the summing function at 44 while delay block 46 again insures the time alignment of the inserted filtered data into the output data stream.

The virtual switch 48 operates in the same manner as before, reversing contacts upon detection of an atrial pace pulse being generated by the implanted CRMD. It remains in position 2 for a predetermined time interval, typically 100–150 ms. The period of time that the switch 48 is feeding the filtered and amplified signal to the ECG output may also be made to terminate with the occurrence of a ventricular pace or a natural ventricular beat or the expiration of the CRMDs programmed AV delay.

Figure 4:
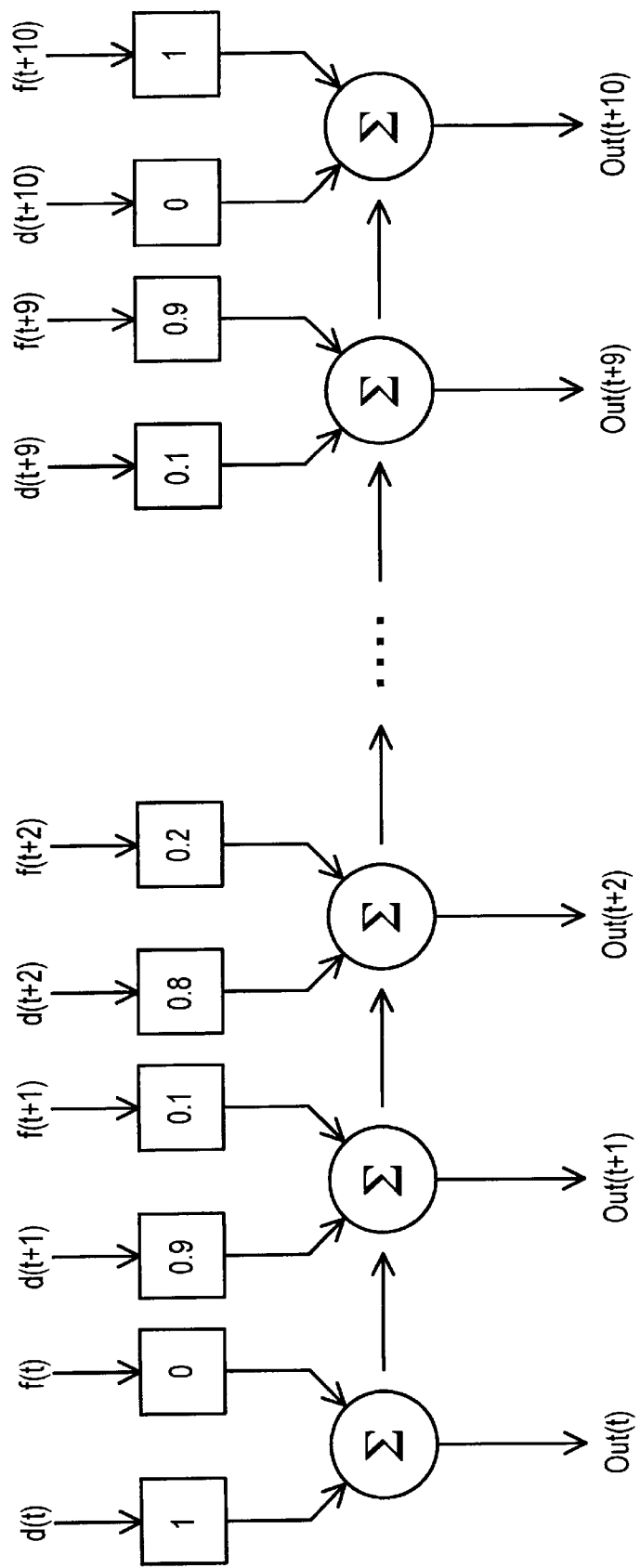
FIG. 4 illustrates the use of a weighted average to smooth transitions between data streams.

FIG. 4 depicts a signal processing approach for smoothing out any transient anomalies occurring upon the detection of an atrial pace pulse when filtered data for enhancing P-wave recognition is inserted into and later removed from the incoming ECG data stream. To ensure a seamless transition between data streams, the digital signal processing algorithm utilized employs a weighted averaging technique for a short period of time at the insertion and removal transition points to smooth out transient anomalies. The algorithm depicted in FIG. 4 is arranged to average a plurality (e.g., 11) consecutive samples of the ECG input developed by the system's A/D converter during the transition from switch position 1 to switch position 2 in the drawings of FIGS. 2 and 3. The first sample, d(t), outputted from delay 28 is multiplied by a factor of 1 and summed with a first sampled output from the channel containing the filter which is multiplied by a factor of 0. Thus, the first sample is unaltered. The second sample d(t+1) is multiplied by a factor 0.9 while the sample exiting the filtered channel is multiplied by a factor of 0.1, with the two being summed to form a smooth result. Ultimately, the $11^{th}$ sample following the transition of the virtual switch from terminal 1 to terminal 2 has the output from the channel containing the delay element multiplied by a factor of 0 before being summed with the $11^{th}$ sample exiting the channel containing the filter element that is multiplied by a factor of 1. At the end of the predetermined time period following the occurrence of an atrial pace, the multiplier coefficients are reversed such that the output from the filtered channel is de-emphasized over nine consecutive samples while the output from the channel containing only the delay receives emphasis.

From what is heretofore been described, it can be seen that the insertion algorithm is dependent upon the presence of an atrial pacing pulse. The atrial pacing pulse can be detected within surface ECG data and discriminated from ventricular pacing pulses to indicate when filtered data should be inserted into the output data stream. If the system is incorporated into a pacemaker/defibrillator programmer, pacing activity information can be relayed from the device, via telemetry. However, detecting the atrial pacing pulses within the surface ECG data is preferable to minimize the delay to the system. It is also a feature of the algorithm that the interval in the ECG trace where P-wave enhancement is occurring be identified, such as by inserting markers or by having the enhanced portion identified by a distinguishing color.

Figure 5:
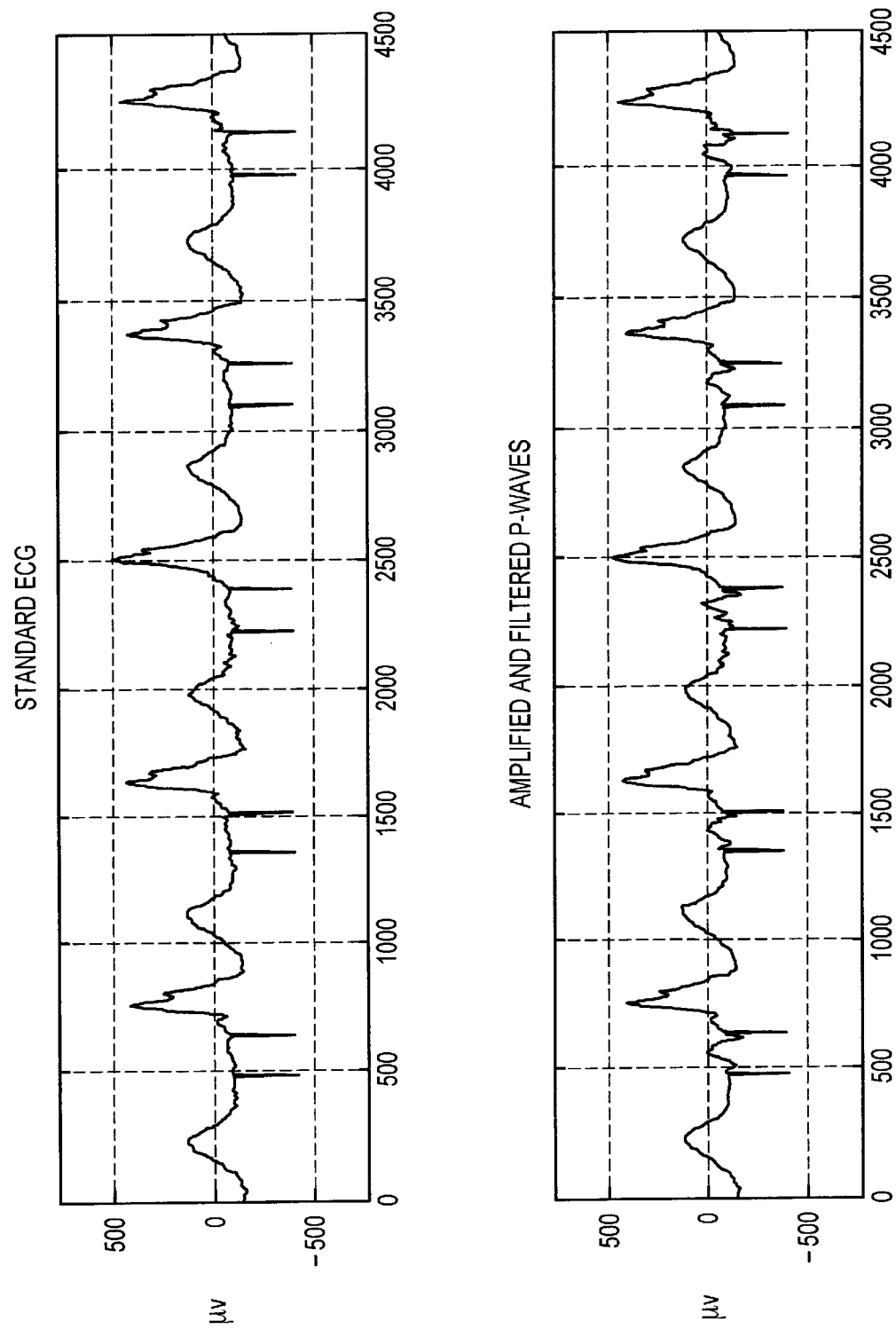
FIG. 5 are ECG traces comparing an enhanced waveform to the enhanced waveform.

FIG. 5 compares the ECG data result after filtering and amplifying P-waves in accordance with the algorithm of FIG. 3 with the raw ECG input signal. Here, a 5 Hz FIR high pass filter 38 removes DC noise from the ECG signal coming from the low pass filter 36. The filter 38 has been found to add a delay of 55 milliseconds, resulting in a total processing delay for the system of 70 ms (delay 46). While 70 ms is a workable value, filters with better computational efficiency may be used to reduce the overall delay value, if desired. In implementing the algorithm, the amplifier 40 had a gain of 5. In comparing the unmodified ECG waveform of FIG. 5A with the ECG data resulting after the filtering and amplifying of the P-waves represented by the trace of FIG. 5B one immediately notes a substantially more visible P-waves in the latter trace.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of enhancing detection of p-waves in an ECG input signal train picked up by surface electrodes affixed to a patient in whom a dual channel CRMD has been implanted, comprising the steps of:
   (a) applying the ECG input signal to first and second signal processing channels, said first channel including a low pass filter having a cut-off frequency capable of attenuating spectral energies characteristic of ventricular depolarization while passing spectral energies characteristic of atrial depolarization, said second channel comprising a signal delay configured to match a signal delay inherent in the low pass filter;
   (b) normally outputting the ECG input signal from the second channel; and
   (c) causing the ECG input signal train exiting the first channel to be presented for a predetermined time following a detection of an atrial pace pulse produced by the CRMD.

2. The method of claim 1 and further including the step of:
   (a) restoring presentation of the input ECG signal train from the second channel following lapse of the predetermined time.

3. The method of claim 2 and further including the step of smoothing out any abrupt changes in the input ECG signal train occasioned by switching between the first and second channels.

4. The method of claim 3 wherein the smoothing step comprises:
   (a) forming a weighted average of a plurality of data samples occurring during a transition of the input ECG signal train between the first and second channels.

5. The method of claim 1 wherein the predetermined time corresponds to a programmed AV delay value of the CRMD.

6. The method of claim 1 wherein the predetermined time begins with a detected atrial paced beat and ends with a ventricular pace or a spontaneous ventricular depolarization, whichever first occurs.

7. The method of claim 1 wherein the ECG signal train exiting the first channel is visually distinguishable from the ECG signal train exiting the second channel.

8. An ecg apparatus for monitoring electrocardiogram (ECG) signals developed between a pair of skin-contacting surface electrodes on a patient in whom a CRMD has been implanted for enhancing the ability to detect atrial depolarization signal components in the ECG signals, comprising:
   (a) means for applying the ECG signals to first and second signal processing channels, the first channel including means for attenuating spectral energies characteristic of ventricular depolarizations while enhancing spectral energies characteristic of atrial depolarizations and the second channel including means for imparting a predetermined delay to the ECG signals flowing therethrough;
   (b) means for normally presenting the ECG signals exiting the second channel; and
   (c) means responsive to detection of an atrial pacing signal from the CRMD for causing the ECG signal exiting the first channel to be presented for a predetermined time following detection of the atrial pacing signal.

9. The apparatus as in claim 8 wherein the means for attenuating comprises a low pass filter having a cut-off frequency of about 30 Hz.

10. The apparatus claim 9 wherein the predetermined delay is approximately a signal delay value equal to that of the low-pass filter.

11. The apparatus of claim 9 and further including a high pass filter in the first channel whose cut-off frequency is less than about 8 Hz.

12. The apparatus of claim 8 wherein the predetermined time is in a range of from about 150 ms to about 200 ms.

13. The apparatus of claim 9 wherein the second channel further includes a high pass filter and an amplifier in series with the low pass filter and means for summing an output of the amplifier with an output of the low pass filter.

14. The apparatus of claim 8 wherein the presentation of the ECG signals exiting the first channel is visually distinguishable from ECG signals exiting the second channel.

15. An ecg apparatus for monitoring ECG signals developed between a pair of skin contacting surface electrodes on a patient in whom a CRMD has been implanted for enhancing the ability to detect atrial depolarization signal components in the ECG signals, comprising:
   (a) a first signal processing channel having a low pass filter for attenuating spectral energies characteristic of ventricular depolarizations and enhancing spectral energies characteristic of atrial depolarizations;
   (b) a second signal processing channel having a delay element; and
   (c) a switch responsive to the generation of an atrial pacing pulse by the CRMD for shifting a presentation of input ECG signals exiting the second channel to the input ECG signal exiting the first channel for a predetermined time interval.

16. The ecg apparatus of claim 15 wherein the low-pass filter has a cut-off frequency of about 30 Hz.

17. The ecg apparatus of claim 15 wherein a time delay of the delay element matches a delay imparted to the signal ECG signals by the low pass filter.

18. The ecg apparatus as in claim 15 wherein the predetermined time interval is equal to a programmed AV delay value of the CRMD.

19. The ecg apparatus as in claim 15 wherein the predetermined time interval begins with the occurrence of the atrial pacing pulse and ends with a paced ventricular beat or an intrinsic ventricular beat whichever is first to occur.

20. The ecg apparatus as in claim 15 wherein the first signal processing channel further includes a high pass filter and an amplifier connected in series with the low pass filter, the high pass filter having a cut-off frequency for removing DC noise from the ECG signals.

21. The ecg apparatus of claim 20 and further including a signal summing device coupled to receive a delayed output from the low pass filter and an amplified output from the high pass filter.

22. The ECG apparatus of claim 15 wherein the presentation of input ECG signals exiting the second channel are rendered visually distinguishable from the input ECG signal exiting the first channel.

* * * * *